(12) United States Patent
Chon (10) Patent No.: US 9,486,360 B2
(45) Date of Patent: Nov. 8, 2016

(54) DUAL ELECTROMAGNETIC COIL VITRECTOMY PROBE

(71) Applicant: Novartis AG, Basel (CH)

(72) Inventor: James Y. Chon, Irvine, CA (US)

(73) Assignee: NOVARTIS AG, Basel (CH)

( * ) Notice: Subject to any disclaimer, the term of this patent is extended or adjusted under 35 U.S.C. 154(b) by 139 days.

(21) Appl. No.: 14/097,295

(22) Filed: Dec. 5, 2013

(65) Prior Publication Data

US 2015/0157503 A1 Jun. 11, 2015

(51) Int. Cl.
*A61B 17/32* (2006.01)
*A61F 9/007* (2006.01)
*A61B 17/00* (2006.01)

(52) U.S. Cl.
CPC .. *A61F 9/00763* (2013.01); *A61B 2017/00398* (2013.01); *A61B 2017/320028* (2013.01)

(58) Field of Classification Search
CPC .......... A61F 9/00736; A61F 9/00763; A61B 17/32002; A61B 17/320016; A61B 2017/320028
See application file for complete search history.

(56) References Cited

U.S. PATENT DOCUMENTS

| | | | |
|---|---|---|---|
| 2,707,389 A | 5/1955 | Fortier | |
| 3,646,727 A | 3/1972 | Wachsmuth | |
| 3,776,238 A * | 12/1973 | Peyman et al. | 606/171 |
| 4,314,560 A | 2/1982 | Helfgott et al. | |
| 4,476,532 A | 10/1984 | Akiyama et al. | |
| 4,533,890 A | 8/1985 | Patel | |
| 4,840,111 A | 6/1989 | Garnjost | |
| 4,940,468 A | 7/1990 | Petillo | |
| 5,275,607 A * | 1/1994 | Lo | A61B 17/32002 604/22 |
| 5,587,536 A | 12/1996 | Rasmussen | |
| 5,643,304 A | 7/1997 | Schechter et al. | |
| 5,716,363 A | 2/1998 | Josephberg | |
| 5,720,742 A | 2/1998 | Zacharias | |
| 5,829,335 A | 11/1998 | Ewald et al. | |
| 5,846,257 A | 12/1998 | Hood | |

(Continued)

FOREIGN PATENT DOCUMENTS

| | | |
|---|---|---|
| CN | 103944346 A | 7/2014 |
| DE | 10247869 A1 | 5/2004 |

(Continued)

OTHER PUBLICATIONS

International Search Report and Written Opinion issued for PCT/US2014/064547, dated Feb. 4, 2015, 13 pgs.

(Continued)

*Primary Examiner* — Melanie Tyson
(74) *Attorney, Agent, or Firm* — Haynes & Boone, LLP (57) ABSTRACT

An ophthalmic surgical system for insertion into an eye of a patient includes a body and a cutting element having a sleeve piece secured to and extending distally from the body, the sleeve piece including a port at an end and an inner piece disposed within the sleeve piece, the inner piece being moveable axially with respect to the sleeve piece. The system further includes a first electromagnetic coil disposed within the body and configured to generate a first magnetic field, a second electromagnetic coil disposed within the body and configured to generate a second magnetic field, a rod piece connected to the inner piece, a first magnetic ring, and a second magnetic ring, the first and second magnetic rings being fixedly secured to the rod piece such that magnetic rings are axially moveable between the first and second electromagnetic coils to open and close the port.

21 Claims, 6 Drawing Sheets

(56) References Cited

U.S. PATENT DOCUMENTS

| | | | |
|---|---|---|---|
| 5,868,728 | A | 2/1999 | Giungo et al. |
| 5,979,494 | A | 11/1999 | Perkins et al. |
| 5,989,262 | A | 11/1999 | Josephberg |
| 6,051,011 | A | 4/2000 | Weidenbenner |
| 6,059,792 | A | 5/2000 | Josephberg |
| 6,221,038 | B1 | 4/2001 | Brisken |
| 6,450,966 | B1 | 9/2002 | Hanna |
| 6,527,736 | B1 | 3/2003 | Attinger et al. |
| 6,575,990 | B1 | 6/2003 | Wang et al. |
| 6,773,445 | B2 | 8/2004 | Finlay et al. |
| 7,335,217 | B2 | 2/2008 | Wang et al. |
| 8,038,692 | B2 | 10/2011 | Valencia et al. |
| 9,101,442 | B2 | 8/2015 | McDonell |
| 2002/0173814 | A1 | 11/2002 | Jung et al. |
| 2003/0078482 | A1 | 4/2003 | Kenan et al. |
| 2003/0195538 | A1 | 10/2003 | Wang et al. |
| 2004/0049217 | A1 | 3/2004 | Ross et al. |
| 2004/0227604 | A1 | 11/2004 | Mitteer et al. |
| 2008/0172077 | A1 | 7/2008 | Valencia et al. |
| 2008/0188881 | A1 | 8/2008 | Chon |
| 2008/0208233 | A1 | 8/2008 | Barnes et al. |
| 2009/0203480 | A1 | 8/2009 | Petzold et al. |
| 2009/0259242 | A1 | 10/2009 | Gerg et al. |
| 2010/0241125 | A1* | 9/2010 | Termanini ............ 606/83 |
| 2011/0144641 | A1 | 6/2011 | Dimalanta, Jr. et al. |
| 2013/0038145 | A1 | 2/2013 | Fujiwara et al. |
| 2013/0144317 | A1 | 6/2013 | Valencia |

FOREIGN PATENT DOCUMENTS

| | | |
|---|---|---|
| DE | 10247869 B4 | 2/2007 |
| EP | 0469641 B1 | 6/1989 |
| EP | 0356372 | 2/1990 |
| EP | 0626628 A1 | 11/1994 |
| EP | 0626628 B1 | 12/1997 |
| EP | 1 110 520 A1 | 6/2001 |
| GB | 2018601 A | 10/1979 |
| GB | 2063579 A | 6/1981 |
| SU | 835 436 A1 | 6/1981 |
| WO | WO 93/05718 | 4/1993 |
| WO | WO 93/05719 | 4/1993 |
| WO | WO 00/78371 A1 | 12/2000 |
| WO | WO 02/041788 A1 | 5/2002 |
| WO | WO 2008/000599 A1 | 1/2008 |
| WO | WO 2008/097755 A2 | 8/2008 |
| WO | WO 2008/097755 A3 | 10/2008 |
| WO | WO 2015/084541 A1 | 6/2015 |
| WO | WO 2016/069277 A1 | 5/2016 |

OTHER PUBLICATIONS

Mark Farley, "Vitrectomy Probe With a Counterbalanced Electromagnetic Drive", U.S. Appl. No. 14/526,718, filed Oct. 29, 2014, 24 pages.

International Searching Authority, International Search Report and Written Opinion, PCT/US2015/055698, Jan. 11, 2016, 12 pages.

* cited by examiner

DUAL ELECTROMAGNETIC COIL VITRECTOMY PROBE

BACKGROUND

The present disclosure relates generally to ophthalmic surgical probes. More particularly, but not by way of limitation, the present disclosure pertains to a dual coil vitrectomy probe.

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina. Therefore, cutting and removal of the vitreous must be done with great care to avoid traction on the retina, the separation of the retina from the choroid, a retinal tear, or, in the worst case, cutting and removal of the retina itself. Delicate operations such as mobile tissue management (e.g., cutting and removal of vitreous near a detached portion of the retina or a retinal tear), vitreous base dissection, and cutting and removal of membranes are particularly difficult.

The use of microsurgical cutting probes in posterior or anterior segments ophthalmic surgery is well known. Such vitrectomy probes are typically inserted via an incision at the cornea or in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Standard vitrectomy probes typically include a hollow needle with a port on the end to pull in vitreous fibrils. An inner cutter piece, placed within the hollow needle, moves back and forth to open and close the port. This operates to cut any fibrils that enter the port while it is open.

Pneumatic mechanisms are typically used to drive commercially available vitrectomy probes. Pneumatic mechanisms, however, have various limitations. First, pneumatic mechanisms are limited in the speed at which they can operate. Accordingly, high cut rates may be unachievable using probes relying on pneumatic actuation. Second, pneumatic mechanisms tend to be noisy, which can be annoying to surgeons and other health care providers doing a surgical procedure. Thus, there is a need for continued improvement in the use and operability of vitrectomy probes. The probes discussed herein are arranged to address one or more of the deficiencies in the prior art.

SUMMARY

This disclosure relates generally to, and encompasses, an apparatus and method for removing ocular tissue and/or fluid from the eye, and more specifically to an ophthalmic surgical probe and methods of using the device to remove ocular tissue and/or fluid from the eye.

According to an illustrative example, an ophthalmic surgical system for treating an eye of a patient includes a body and a cutting element extending distally from the body. The cutting element includes a sleeve piece comprising a port at an end and an inner piece disposed within the sleeve piece, the inner piece being moveable axially with respect to the sleeve piece to open and close the port. The probe further includes a first electromagnetic coil disposed within the body and configured to generate a first magnetic field, a second electromagnetic coil disposed within the body and configured to generate a second magnetic field, a first magnetic ring moveable by the first magnetic field when the first electromagnetic coil generates the first magnetic field, and a second magnetic ring moveable by the second magnetic field when the second electromagnetic coil generates the second magnetic field, the first and second magnetic rings being fixedly secured relative to the inner piece such that movement of the first and second magnetic rings moves the inner piece and opens and closes the port.

According to an illustrative example, an ophthalmic surgical system includes a probe having a body, a sleeve piece extending distally from the body, and an actuator assembly secured to the body. The actuator assembly includes a first electromagnetic coil and a second electromagnetic coil disposed coaxially with respect to the first electromagnetic coil. The probe further includes an armature assembly having a rod piece having a needle portion disposed within the sleeve piece, the needle portion being movable axially with respect to the sleeve piece, a first magnetic ring secured to the rod piece, and a second magnetic ring secured to the rod piece, wherein the first and second magnetic rings are positioned along the rod piece such that they are between the first and second electromagnetic coils. The system further includes a controller arranged to apply an electrical signal to the actuator assembly to move the armature assembly with respect to the actuator assembly.

According to an illustrative example, a method for using a vitrectomy probe includes applying a first signal to a first electromagnetic coil and a second electromagnetic coil disposed within a body of a surgical probe, the first signal creating an electromagnetic field that applies a first force in a first direction on an armature assembly moveable within the body to displace an inner piece of a cutting element relative to an outer sleeve of the cutting element to open or close a port in the outer sleeve, the armature assembly comprising a first magnetic ring and a second magnetic ring. The method further includes applying a second signal to the first and second electromagnetic coils to move the armature assembly in a second direction that is opposite of the first direction to displace the inner piece of a cutting element relative to the outer sleeve of the cutting element to open or close a port in the outer sleeve.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to apparatuses, systems, and methods for removing ocular tissue and/or fluid from the eye. The various figures show embodiments of an exemplary ophthalmic surgical probe and methods of using the device to remove ocular tissue and/or fluid from a patient's eye. One of ordinary skill in the art, however, would understand that similar embodiments could be used to remove tissue and/or fluid from other locations in the body without departing from the general intent or teachings of the present disclosure.

Figure 1:
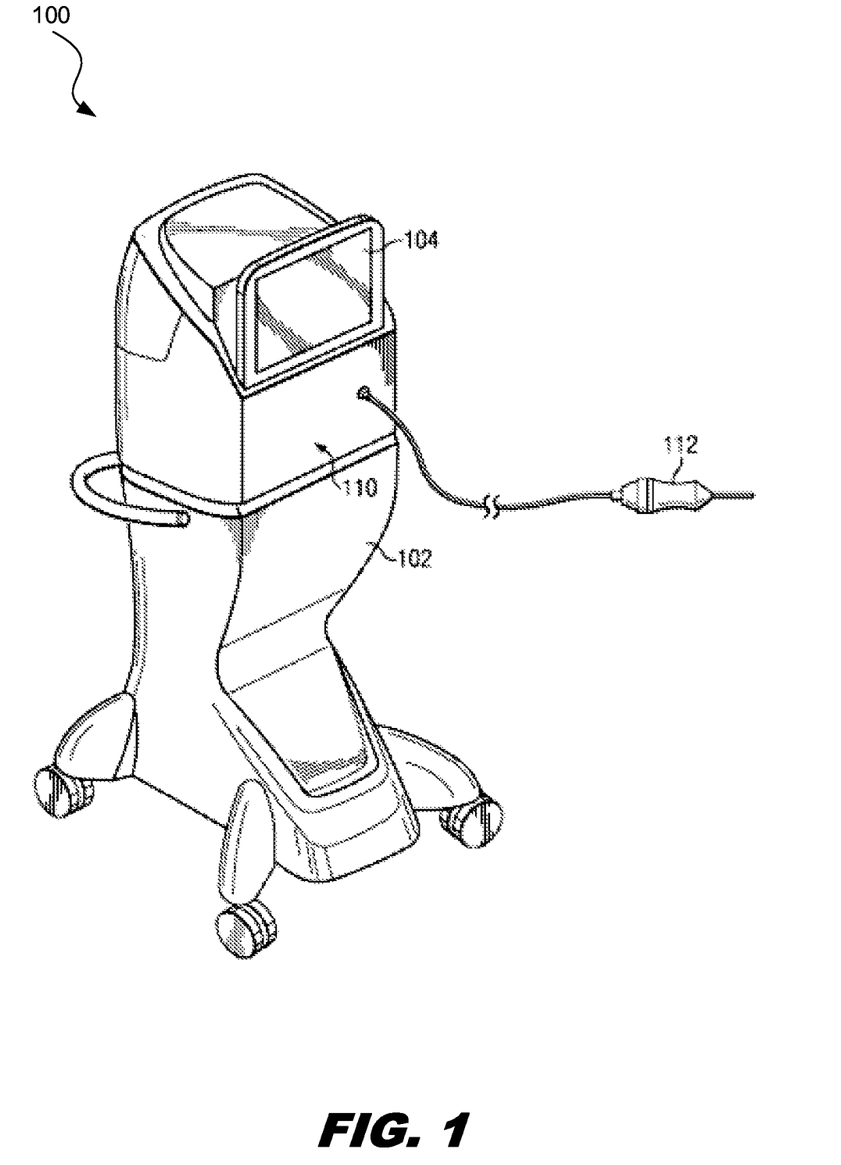
FIG. 1 is a diagram showing an illustrative vitrectomy probe system according to one example incorporating the principles described herein.

FIG. 1 is a diagram showing an illustrative vitrectomy surgical system 100. According to the present example, the vitrectomy surgical system 100 includes a base housing 102, console 110, and an associated display screen 104 showing data relating to system operation and performance during a vitrectomy surgical procedure. In this exemplary embodiment, the vitrectomy surgical system 100 is a mobile console that may be used by a health care provider to perform a vitrectomy surgical procedure. The vitrectomy surgical system 100 includes a vitrectomy probe 112 and is configured to be used during an ophthalmic surgical procedure, such as, for example, a vitrectomy surgical procedure. The base housing 102/console 110 may be configured to process, receive, and store data and provide signals to the vitrectomy probe and/or the display 104.

Figure 2:
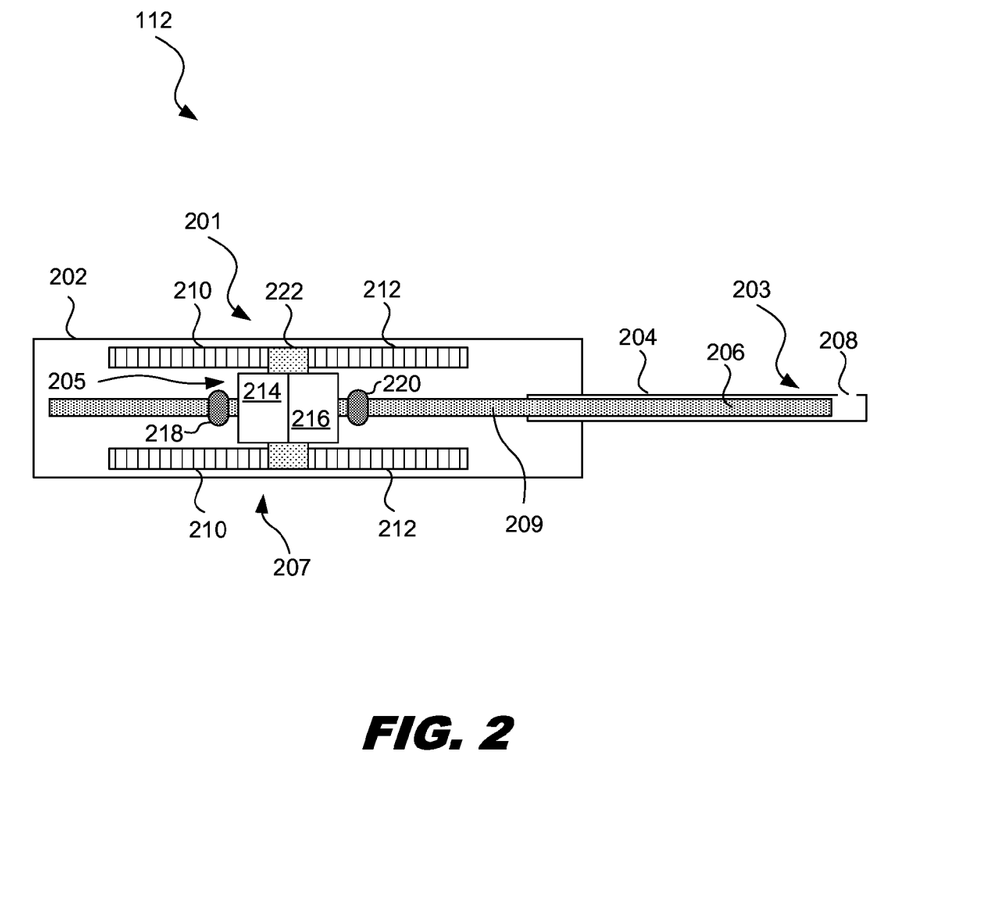
FIG. 2 is a diagram showing an illustrative vitrectomy probe with dual coils according to one example incorporating the principles described herein.

FIG. 2 is a stylized diagram showing the illustrative vitrectomy probe 112 with dual electromagnetic coils 210, 212. FIG. 2 is a cross-sectional diagram along the center of the vitrectomy probe 112. According to the present example, the vitrectomy probe 112 includes a body 202. The body 202 includes a drive mechanism 201, which includes an actuator assembly 207 and an armature assembly 205. The vitrectomy probe 112 also includes a cutting element 203 that includes a sleeve piece 204 and an inner piece 206.

The body 202 may be made from a variety of materials commonly used to form such tools. For example, the body 202 may be made of a lightweight aluminum or plastic. The exterior portion of the body 202 may be ergonomically designed for comfortable grasping by a surgeon or operator of the vitrectomy probe 112. The inner portion of the body 202 is designed to support the dual electromagnetic coils 210, 212, stopping mechanisms 218, 220, and sleeve piece 204.

The cutting element 203 includes the inner piece 206 and the sleeve piece 204. The sleeve piece 204 is a hollow needle designed to enter a patient's eye. The sleeve piece 204 includes the port 208 at the distal end. The port 208 is disposed along the side of the distal end as illustrated. The port 208 may be a square, rectangular, circular, elliptical, or other shaped opening. The opening is designed to allow vitreous fibrils from the patient's eye to enter. Movement of the inner piece 206 within the sleeve piece 204 operates to open and close the port 208, thereby cutting any vitreous fibrils that enter the port 208 while it is open.

The inner piece 206 of the cutting element 203 operates as the cutter portion of the vitrectomy probe 112. Thus, the end of the inner piece 206 is sufficiently sharp so that it can cut the vitreous fibrils. The inner piece 206 may be made from a variety of materials such as stainless steel. In some cases, the inner piece 206 may include multiple pieces attached together. For example, the distal end of the inner piece 206 may be a cutter piece made of a different material than the proximal end. The proximal end of the inner piece 206 may be connected to, or be part of, the armature assembly 205.

The armature assembly 205 includes a first magnetic ring 214 and a second magnetic ring 216 attached to a rod piece 209. The rod piece 209 is connected to the inner piece 206 of the cutting element 203. In some embodiments, the rod piece 209 and the inner piece 206 may be one contiguous piece.

The magnetic rings, 214, 216 may be made of a permanent magnetic material such as a ferromagnetic material. The magnetic rings 214, 216 are positioned between two stopping mechanisms 218, 220 that prevent the magnetic rings 214, 216 from moving beyond a position between the two electromagnetic coils 210, 212 of the actuator assembly 207. Movement of the magnetic rings 214, 216 between the two stopping mechanisms 218, 220 operates to open and close the port 208 at the end of the sleeve piece 204.

The stopping mechanisms 218, 220 are used to prevent the armature assembly 205 from moving beyond its intended range of movement. Specifically, when the magnetic rings 214, 216 are pushed up against the first stopping mechanism 218, the port 208 is open. Conversely, when the magnetic rings 214, 216 are pushed up against the second stopping mechanism 220, the port 208 is closed. The stopping mechanisms 218, 220 may be made of an elastomeric material that provides some level of damping, such as rubber, silicone, or other material. Such materials may help reduce the noise made by the vitrectomy probe 112 while operating and thus may be referred to as noise reduction materials. In some embodiments, the stopping mechanisms 218, 220 may be made of materials that do not dampen sound.

In some examples, the position of the stopping mechanisms 218, 220 may be adjustable relative to the body 202 and the sleeve piece 204. Thus, an operator may make adjustments to the probe to change the open and closed positions of the port 208. This may be beneficial for various surgical related reasons.

The actuator assembly 207 includes a first electromagnetic coil 210 and a second electromagnetic coil 212 placed within the body 202 along a common axis. The electromagnetic coils 210, 212 are placed within the body 202 on opposing sides of an adjacent spacer 222. The electromagnetic coils 210, 212 may be formed by winding a conductive wire into a solenoid formation. When an electric current is applied to such a formation, a magnetic field is created in the center of the coil. The direction of the magnetic field is based on the direction of the electric current flowing through the wire.

In one example, the electromagnetic coils may be formed by about 1500 turns of 36 gauge wires. Other formations of the electromagnetic coils may also be used in accordance with principles described herein. For example, some electromagnetic coils have between about 1800 to 2000 turns with a wire gauge of about 26-46 gauge. Still other formations are contemplated. The voltage level used to drive the electromagnetic coils may vary based on the specifications of the electromagnetic coils 210, 212 and the magnetic rings 214, 216.

Operation of the vitrectomy probe 112 will now be discussed. The magnetic rings 214, 216 may be positioned such that a current applied to the first electromagnetic coil 210 puts a force on the first magnetic ring 214. Additionally, an electric current applied to the second electromagnetic coil 212 puts a force on the second magnetic ring 216. The electric current signals applied to the electromagnetic coils 210, 212 are such that while the first electromagnetic coil 210 pushes on the first magnetic ring 214, the second electromagnetic coil 212 pulls on the second magnetic ring 216 to displace the first and second magnetic rings 214, 216, along with the attached inner piece 206 in the distal direction. Conversely the second electromagnetic coil 212 pushes on the second magnetic ring 216 and the first electromagnetic coil 210 pulls on the first magnetic ring 214 to displace the first and second magnetic rings 214, 216, along with the attached inner piece 206 in the proximal direction.

Figure 3:
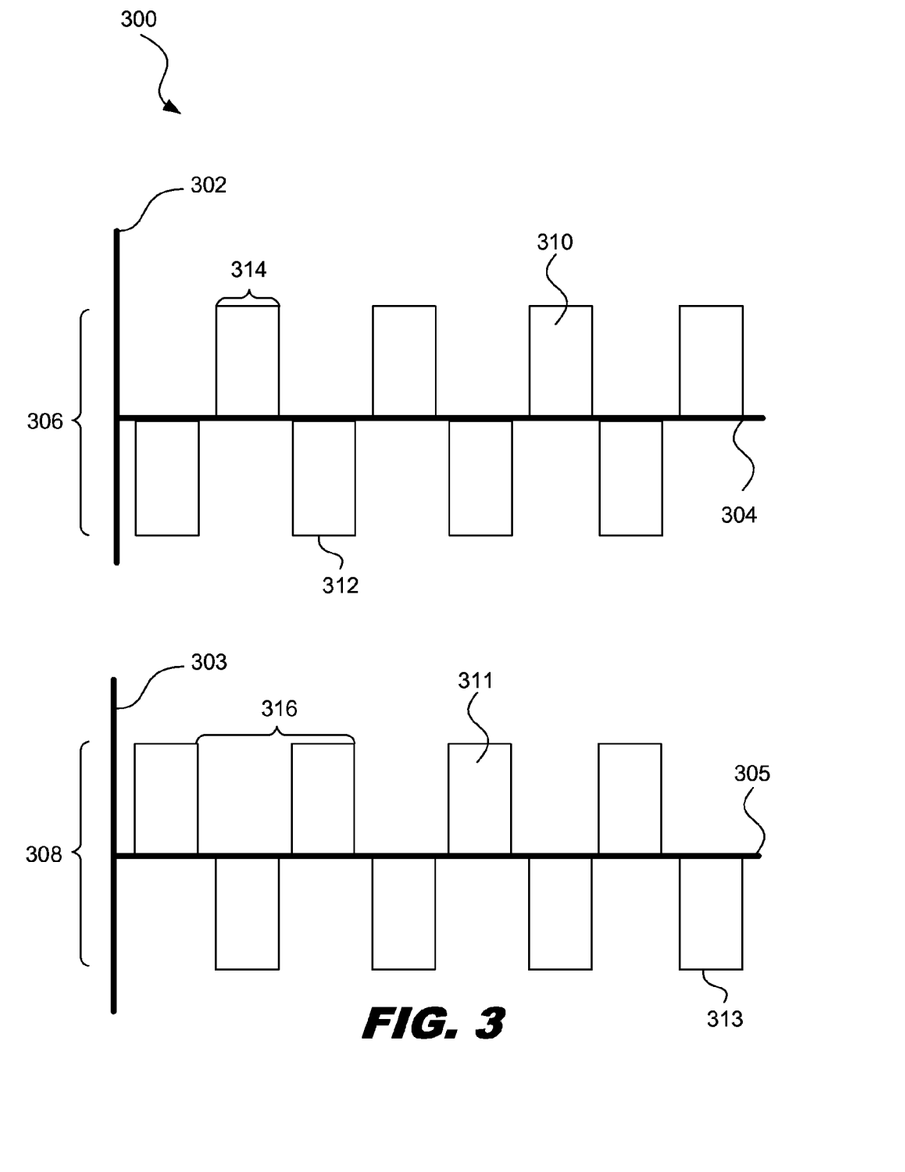
FIG. 3 is a diagram showing illustrative waveforms used to drive the vitrectomy probe according to one example incorporating the principles described herein.

FIG. 3 is a diagram showing illustrative waveforms 300 used to drive the vitrectomy probe 112. According to the present example, the vertical axis 302, 303 represents the strength of a signal, such as in terms of voltage or current. The horizontal axes 304, 305 represent time. The first horizontal axis 304 represents a first electric signal 306 that can be applied to one of the two electromagnetic coils 210, 212 illustrated in FIG. 2. The second horizontal axis 305 represents a second electric signal 308 that can be applied to the other one of the electromagnetic coils 210, 212.

The first signal 306 includes a series of positive pulses 310 and a series of negative pulses 312. In this example, the positive pulses 310 cause a magnetic field within the respective electromagnetic coil that pushes on the armature assembly 205, which includes the two magnetic rings as illustrated in FIG. 2. The negative pulses 312 cause a pulling force on the armature assembly 205. Thus, a particular electromagnetic coil alternates between pushing and pulling on the armature assembly 205.

The second signal 308 also includes a series of positive pulses 311 and a series of negative pulses 313. In this example, the positive pulses 311 cause a magnetic field within the respective electromagnetic coil that pushes on the armature assembly 205, which includes the two magnetic rings 214, 216 as illustrated in FIG. 2. The negative pulses 313 cause a pulling force on the armature assembly 205.

The timing of the signals 306, 308 is such that one of the electromagnetic coils 210, 212 pushes on the armature assembly 205 while the other electromagnetic coil pulls on the armature assembly 205. By doing so, the energy requirements to drive the probe are reduced. This also reduces the self-heating temperature rise during operation of the probe.

The electric signals 306, 308 are pulse waveforms. The strength of the pulses may be based on the specifications of the electromagnetic coils 210, 212, such as the number of windings and gauge size, as well as the force needed to move the armature assembly 205 as desired. The pulse width 314 may also be based on the force needed to move the armature assembly 205 from one point to another. In one example, the pulse width may be within a range of 1.2 and 2.0 milliseconds. In a more specific example, the pulse width may be approximately 1.6 milliseconds. Other pulse widths are contemplated. The width of the pulses may also be selected based on the force necessary to overcome the static friction between the inner piece and the sleeve piece.

The wavelength 316 of the signals 306, 308 is directly related to the frequency at which the signals 306, 308 operate. The frequency may be adjusted to set the rate at which the probe cuts the vitreous fibrils. The rate may be defined as cuts per minute. For example, the frequency may be adjusted to set the probe to cut at a rate of 7,000 to 15,000 cuts per minute. In a more specific example, the vitrectomy probe 112 may be set to cut at a rate between about 9,000 to 12,000 cuts per minute, and more specifically, the vitrectomy probe 112 may operate at 10,000 cuts per minute. For example, to operate at 10,000 cuts per minute, the frequency of the signals is set to approximately 168 hertz (Hz).

In some examples, the signals 306, 308 may include a holding signal (not shown). The holding signal is applied to the electromagnetic coils 210, 212 after the armature assembly 205 reaches its final position. The holding signal holds the armature assembly 205 in place against one of the stopping mechanisms 218, 220 until it is time to move the armature assembly 205 to a position against the other one of the stopping mechanisms 218, 220. The strength of the holding signal may depend on what force is necessary to hold the armature assembly 205 in place for the desired time period. In some cases, the strength of the holding signal may be less than the strength of the pulses that initially move the armature assembly 205 to a different position.

Figure 4A:
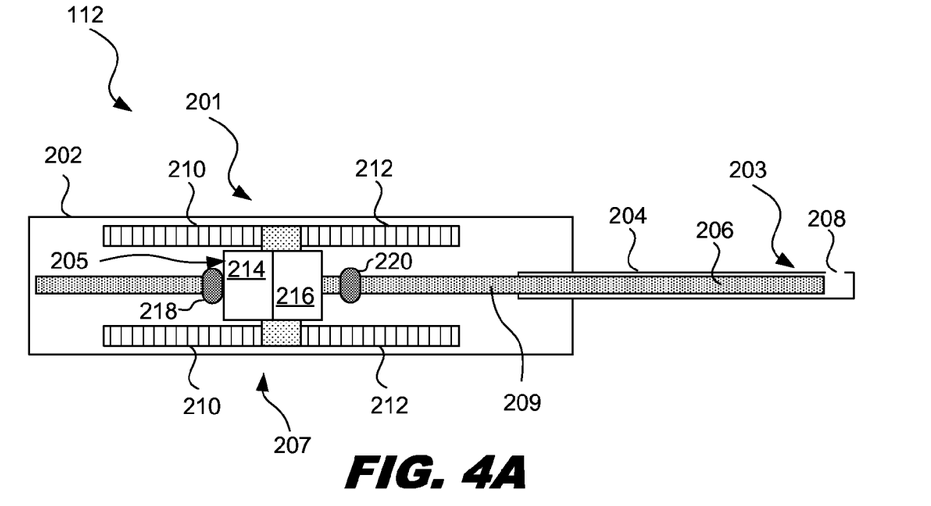
FIGS. 4A and 4B are diagrams showing the vitrectomy probe at different stages of a cycle according to one example incorporating the principles described herein.
Figure 4B:
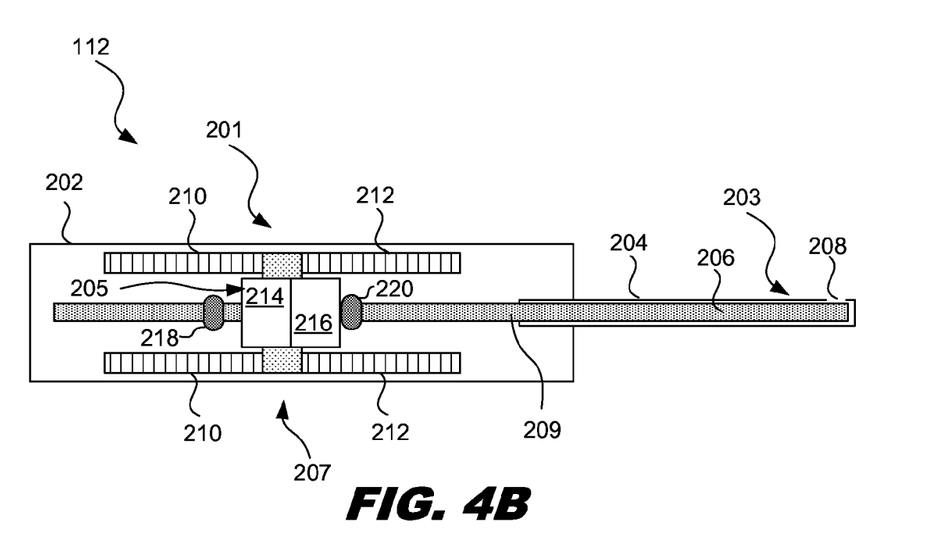

FIGS. 4A and 4B are diagrams showing the vitrectomy probe 112 at different stages of a cycle. According to the present example, FIG. 4A is a diagram showing the armature assembly 205 in a first position against the first stopping mechanism 218. FIG. 4B is a diagram showing the armature assembly 205 in a second position against stopping mechanism 220.

To move the armature assembly 205 into the first position as illustrated in FIG. 4A, the first electromagnetic coil 210 provides a pulling force on the first magnetic ring 214 while the second electromagnetic coil 212 provides a pushing force on the second magnetic ring 216. The optional holding signal may then hold the armature assembly 205 so that the first magnetic ring 214 is pressed against the first stopping mechanism 218. While in this position, the inner piece 206 is positioned so that the port 208 is open and vitreous fibrils are able to enter into the hollow sleeve piece 204.

To move the armature assembly 205 into the second position as illustrated in FIG. 4B, the second electromagnetic coil 212 provides a pulling force on the second magnetic ring 216 while the first electromagnetic coil 210 provides a pushing force on the first magnetic ring 214. The optional holding signal may then hold the armature assembly 205 so that the second magnetic ring 216 is pressed against the second stopping mechanism 218. While moving into this position, the inner piece 206 closes the port 208, and thereby cuts any vitreous fibrils that have entered the port 208. The vitreous fibers may then be aspirated through the inner piece 206 and out of the patient's eye.

During operation, the armature assembly 205 moves rapidly back and forth to open and close the port 208, thereby cutting the vitreous fibrils within the patient's eye. In some exemplary embodiments, the total distance between the extreme positions of the armature assembly 205 may be within a range of 0.03 and 0.05 inches. In a more specific example, the total distance between the extreme positions is approximately 0.04 inches. Other distances, both larger and smaller are contemplated.

Figure 5:
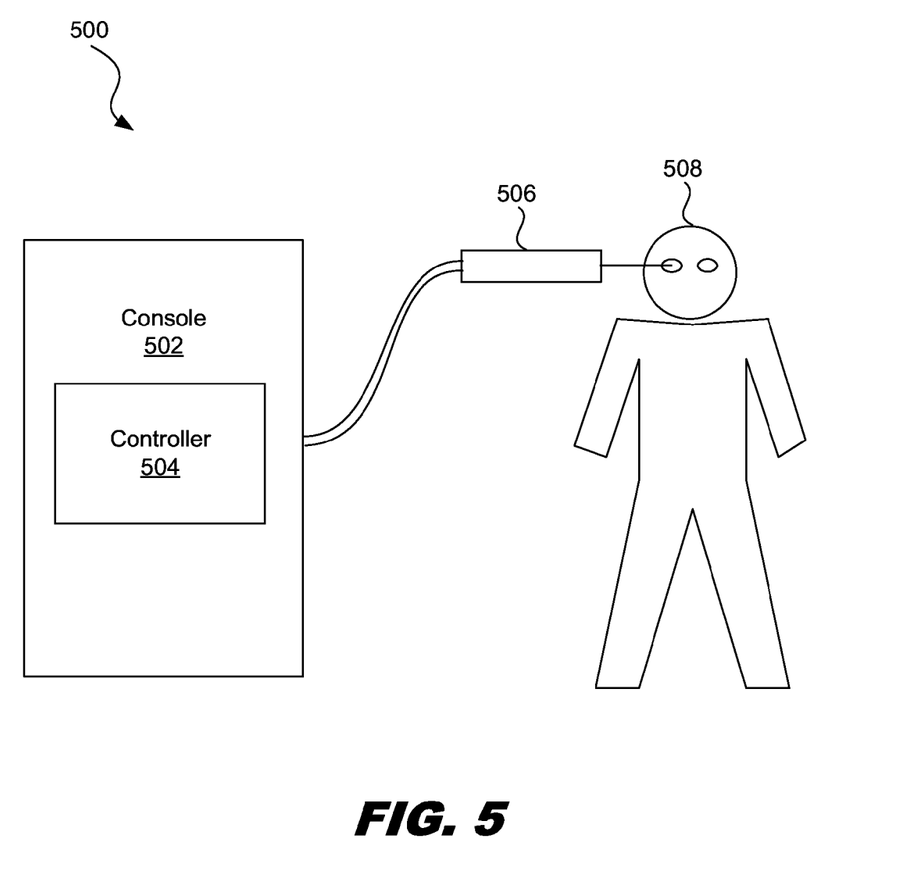
FIG. 5 is a diagram showing illustrative components of a vitrectomy probe with respect to a patient according to one example incorporating the principles described herein.

FIG. 5 is a diagram showing illustrative components of a vitrectomy surgical system 500 with respect to a patient 508. According to the present example, the system 500 includes a console 502 and a hand piece 506. The console 502 includes a controller 504. The hand piece 506 may be the same probe 112 discussed above, or may be another probe used by an operator or surgeon to treat a condition of the eye. In this example, the distal portion is inserted into the eye of a patient 508.

The console 502 includes all the necessary components to drive and work with the hand piece 506. Additional components and features of the console would be apparent to one of ordinary skill in the art. The controller 504 within the console 502 provides the desired electrical signals to the hand piece 506. These signals may be adjusted by the operator based on surgical parameters, surgeon preference, patient condition, or other factors related to the eye of the patient 508.

Figure 6:
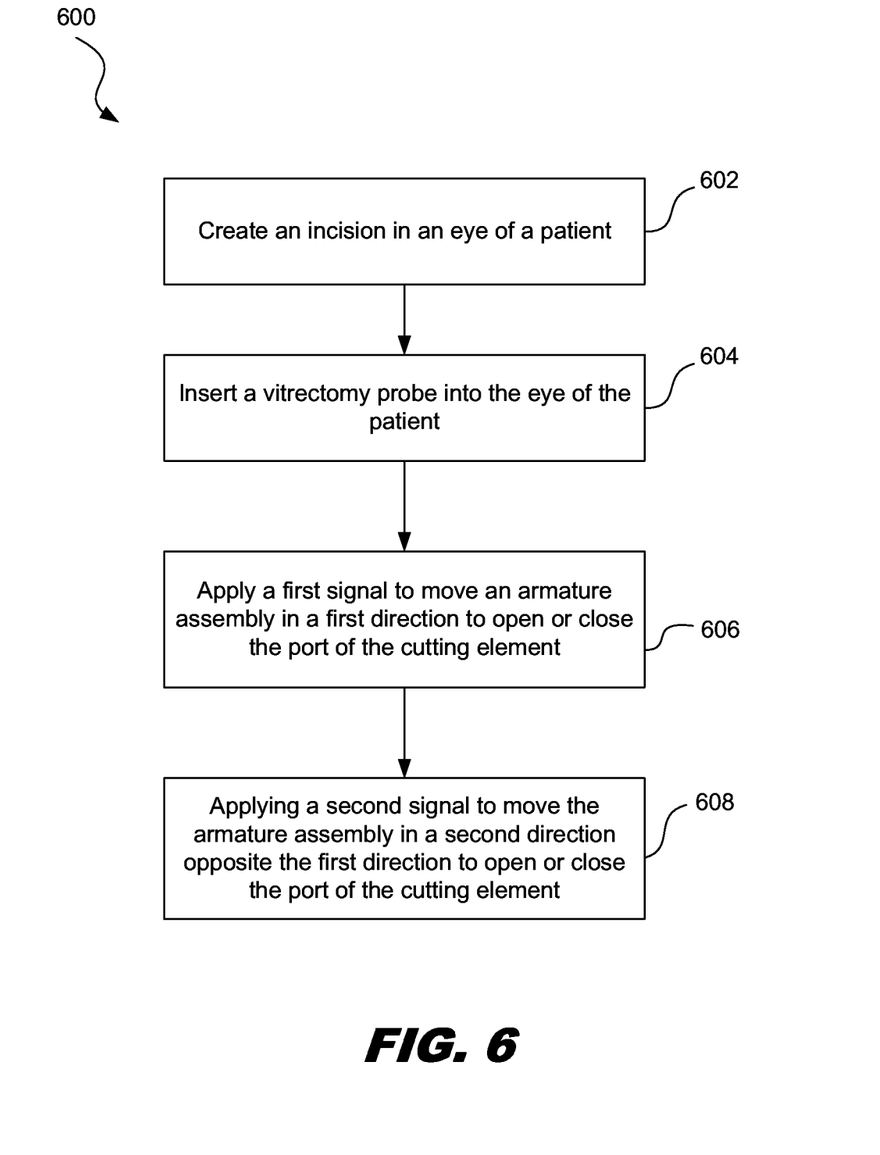
FIG. 6 is a flowchart showing an illustrative method for treating a patient with a dual coil vitrectomy probe according to one example incorporating the principles described herein.

FIG. 6 is a flowchart showing an illustrative method 600 for treating a patient with a dual coil vitrectomy probe. According to the present example, the method creating an incision in an eye of a patient at a step 602. At step 604, the method 600 includes inserting a vitrectomy probe into the eye of the patient. In some aspects, the probe includes the armature assembly described above having the first magnetic ring and the second magnetic ring, and includes a cutting element having a hollow sleeve piece extending distally from the body and an inner piece within the hollow sleeve piece attached to the armature assembly.

At a step 606, the method 600 includes applying a first signal to move an armature assembly in a first direction to open or close the port of the cutting element. The first signal may be generated at the controller and may be applied to a first electromagnetic coil and a second electromagnetic coil disposed within the body. It may be applied to one of the first and second electromagnetic coils simultaneously or it may be applied to the first and second electromagnetic coils in an alternating manner. The first signal creates an electromagnetic field that applies a first force in a first direction on the armature assembly. The electromagnetic field acts on one or both of the first and second magnetic rings forming a part of the armature assembly. Because of this force, the armature assembly physically displaces relative to the coils, and in the embodiments disclosed herein, moves in a distal or proximal direction relative to the electromagnetic coils. The inner piece of the cutting element, which is connected to the armature assembly, moves with the armature assembly in the distal or proximal direction within the inner piece. The movement opens or closes the port formed in the distal portion of the hollow sleeve piece.

At a step 608, the method 600 includes applying a second signal to move the armature assembly in a second direction opposite the first direction to either open or close the port of the cutting element. Applying the second signal may include applying a signal to the first and second electromagnetic coils to move the armature assembly in a second direction that is opposite of the first direction. Similar to the description above at step 606, this creates an electromagnetic field that acts on one or both of the first and second magnetic rings forming a part of the armature assembly. However, the second signal creates a magnetic field having a direction opposite the direction of the magnetic field created at step 606. Therefore, this field acts on the magnetic rings to move the armature assembly in the direction opposite that of step 606 to open the port if was closed at step 606 or to close the port if was opened at step 606. As described above, the cutting rate is dependent on the frequency of the first and second signals, which in turn, open and close the port in the cutting element.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An ophthalmic surgical system for treating an eye of a patient, the system comprising:
    a body;
    a cutting element extending distally from the body including:
        a sleeve piece comprising a port at an end; and
        an inner piece disposed within the sleeve piece, the inner piece being moveable axially with respect to the sleeve piece to open and close the port;
    a first electromagnetic coil disposed within the body and configured to generate a first magnetic field in response to a first signal having a first polarity;
    a second electromagnetic coil disposed within the body and configured to generate a second magnetic field in response to a second signal having a second polarity opposite the first polarity, the first and second signals configured to be applied simultaneously;
    a first magnetic ring moveable by the first magnetic field when the first electromagnetic coil generates the first magnetic field; and
    a second magnetic ring moveable by the second magnetic field when the second electromagnetic coil generates the second magnetic field, the first and second magnetic rings being fixedly secured relative to the inner piece without an electromagnetic coil directly therebetween such that movement of the first and second magnetic rings moves the inner piece and opens and closes the port.

2. The system of claim 1, wherein the first and second magnetic rings are disposed at least partially in an interior of the first and second electromagnetic coils.

3. The system of claim 1, further comprising a controller configured to apply an electric signal to the first and second electromagnetic coils such that while the first electromagnetic coil applies a pushing force on the first magnetic ring, the second electromagnetic coil applies a pulling force on the second magnetic ring.

4. The system of claim 3, wherein the electric signal comprises a pulse waveform.

5. The system of claim 4, wherein the controller is configured to generate an electrical signal comprising a pulse waveform having a frequency causing the port to open and close at a rate within a range of 7,000 and 15,000 cuts per minute.

6. The system of claim 3, wherein the controller is further configured to apply a holding signal to the first and second electromagnetic coils to generate an electromagnetic field on the magnetic rings to hold the inner piece in either an open position or a closed position.

7. The system of claim 1, comprising a rod piece connected to the inner piece, the first and second magnetic rings being fixedly secured to the rod piece.

8. The system of claim 1, further comprising a first stopping mechanism and a second stopping mechanism, the first and second stopping mechanisms being disposed on opposing sides of the first and second magnetic rings, the first and second stopping mechanisms being secured to the body to limit movement of the inner piece to movement needed to open and close the port.

9. The system of claim 8, wherein the first and second stopping mechanisms comprise a noise reduction material.

10. The system of claim 1, wherein the inner piece is movable between a first position and a second position, the distance between the positions being within a range of 0.03 and 0.05 inches.

11. The system of claim 1, wherein the first and second magnetic rings are adjacent and have a polarity in the same direction.

12. An ophthalmic surgical system comprising:
a probe comprising:
a body;
a sleeve piece extending distally from the body;
an actuator assembly secured to the body, the actuator assembly comprising;
a first electromagnetic coil; and
a second electromagnetic coil disposed coaxially with respect to the first electromagnetic coil;
an armature assembly comprising:
a rod piece having a needle portion disposed within the sleeve piece, the needle portion being movable axially with respect to the sleeve piece;
a first magnetic ring secured to the rod piece; and
a second magnetic ring secured to the rod piece, wherein the first and second magnetic rings are positioned along the rod piece without an electromagnetic coil directly therebetween such that the first and second magnetic rings are between the first and second electromagnetic coils; and
a controller arranged to simultaneously apply a first electrical signal to the first electromagnetic coil and a second signal to the second electromagnetic coil to move the armature assembly with respect to the actuator assembly, the second signal having a polarity opposite of the first signal.

13. The probe of claim 12, wherein the sleeve piece comprises a port to allow in vitreous fluid from a patient's eye.

14. The probe of claim 13, wherein the rod piece is configured to move relative to the sleeve piece.

15. The probe of claim 12, wherein the controller is arranged to apply an electrical signal comprising a first current to the first electromagnetic coil to cause a first force on the first magnetic ring in a first direction and simultaneously apply a second current to the second electromagnetic ring to cause a force on the second magnetic ring in the first direction.

16. The probe of claim 12, wherein the controller is arranged to apply an electrical signal comprising a first current to the first electromagnetic coil to cause a first force on the first magnetic ring in a first direction and alternatingly apply a second current to the second electromagnetic ring to cause a force on the second magnetic ring in a second direction, the second direction being opposite of the first direction.

17. The probe of claim 12, wherein the electrical signal has a pulse waveform.

18. The probe of claim 17, wherein the pulse waveform has a frequency set to cause the port to open and close at a rate within a range of 7,000 and 15,000 cuts per minute.

19. The probe of claim 17, wherein a width of the pulse waveform ranges between 1.2 and 2.0 milliseconds.

20. A method for using a vitrectomy probe, the method comprising,
applying a first signal having a first polarity to a first electromagnetic coil and a second signal having a second polarity opposite the first polarity to a second electromagnetic coil disposed within a body of a surgical probe, the first and second signals creating an electromagnetic field that applies a first force in a first direction on an armature assembly moveable within the body to displace an inner piece of a cutting element relative to an outer sleeve of the cutting element to open or close a port in the outer sleeve, the armature assembly comprising a first magnetic ring and a second magnetic ring positioned without an electromagnetic coil directly therebetween; and
applying a third and fourth signal to the first and second electromagnetic coils to move the armature assembly in a second direction that is opposite of the first direction to displace the inner piece of a cutting element relative to the outer sleeve of the cutting element to open or close a port in the outer sleeve.

21. The method of claim 20, wherein the first and second signals comprise pulse waveforms.

\* \* \* \* \*